(12) United States Patent
Aneas (10) Patent No.: US 10,729,854 B2
(45) Date of Patent: Aug. 4, 2020

(54) HOUSING FOR MOUNTING A CONTAINER ON AN INJECTION PEN, ASSEMBLY FORMING AN INJECTABLE PRODUCT RESERVOIR FOR AN INJECTION PEN AND INJECTION PEN EQUIPPED WITH SUCH AN ASSEMBLY

(71) Applicant: BIOCORP PRODUCTION, Issoire (FR)

(72) Inventor: Antoine Aneas, Menetrol (FR)

(73) Assignee: BIOCORP PRODUCTION, Issoire (FR)

( * ) Notice: Subject to any disclaimer, the term of this patent is extended or adjusted under 35 U.S.C. 154(b) by 300 days.

(21) Appl. No.: 15/579,087

(22) PCT Filed: Jun. 1, 2016

(86) PCT No.: PCT/EP2016/062395
§ 371 (c)(1),
(2) Date: Dec. 1, 2017

(87) PCT Pub. No.: WO2016/193314
PCT Pub. Date: Dec. 8, 2016

(65) Prior Publication Data
US 2018/0169339 A1 Jun. 21, 2018

(30) Foreign Application Priority Data

Jun. 2, 2015 (FR) ..................... 15 54993

(51) Int. Cl.
*A61M 5/24* (2006.01)
*A61J 1/16* (2006.01)
*A61M 5/34* (2006.01)

(52) U.S. Cl.
CPC .............. *A61M 5/24* (2013.01); *A61J 1/16* (2013.01); *A61M 5/347* (2013.01);
(Continued)

(58) Field of Classification Search
CPC ............ A61M 5/24; A61M 2005/2407; A61M 2005/244; A61M 2005/2433; A61M 2005/2437; A61M 2005/2444; A61J 1/16
See application file for complete search history.

(56) References Cited

U.S. PATENT DOCUMENTS 8,801,679 B2    8/2014  Iio et al.
2004/0074076 A1 4/2004  Landau
(Continued)

FOREIGN PATENT DOCUMENTS

CN    102917740 A   2/2013
CN    104185488 A   12/2014
(Continued)

OTHER PUBLICATIONS

French Search Report issued for French Application No. FR 15 54993 dated Mar. 17, 2016.
(Continued)

*Primary Examiner* — Nathan R Price
*Assistant Examiner* — Anh Bui
(74) *Attorney, Agent, or Firm* — Pearne & Gordon LLP (57) ABSTRACT

The housing for mounting an elongate-shaped container on an injection pen comprises an elongate-shaped body which extends along a longitudinal axis (X30) and which defines an interior volume (V32) for fully receiving the container. The body is provided, on the outside of a first axial end, with at least one first mechanical member for attaching a needle. The body is further provided, in the vicinity of a second axial end opposite the first axial end, with at least one second mechanical member for attaching the housing onto an injection pen. The housing further comprises, in the vicinity of the first axial end thereof, at least one third mechanical member for irreversibly locking a container in position, fully contained in the interior volume (V32) of the body of the
(Continued)

housing. Said third locking member is formed by an elastically deformable tab intended to ensure locking of the container in position in the interior volume (V32) of the body of the housing, by axially retaining a flange of the container.

15 Claims, 8 Drawing Sheets

(52) U.S. Cl.
CPC .................. *A61M 2005/244* (2013.01); *A61M 2005/2407* (2013.01); *A61M 2005/2411* (2013.01); *A61M 2005/2477* (2013.01); *A61M 2005/2488* (2013.01); *A61M 2005/2492* (2013.01)

(56) References Cited

U.S. PATENT DOCUMENTS

| 2013/0046245 A1* | 2/2013 | Raab | A61M 5/24 604/187 |
|---|---|---|---|
| 2013/0220869 A1 | 8/2013 | Klintenstedt et al. | |
| 2014/0066863 A1* | 3/2014 | Nzike | A61M 5/14566 604/228 |
| 2014/0358093 A1 | 12/2014 | Soerensen et al. | |
| 2015/0011949 A1 | 1/2015 | Soerensen | |

FOREIGN PATENT DOCUMENTS

| EP | 2253348 A1 | 11/2010 |
|---|---|---|
| JP | 2006502803 A | 1/2006 |
| JP | 2013517870 A | 5/2013 |
| JP | 2015507983 A | 3/2015 |
| JP | 2018516685 A | 6/2018 |
| WO | 2004035107 A2 | 4/2004 |
| WO | 2009125582 A1 | 10/2009 |
| WO | 2011/092326 A1 | 8/2011 |
| WO | 2011/124631 A1 | 10/2011 |
| WO | 2011124632 A1 | 10/2011 |
| WO | 2012/017063 A2 | 2/2012 |
| WO | 2013/124118 A1 | 8/2013 |
| WO | 2013124119 A1 | 8/2013 |
| WO | 2015011001 A1 | 1/2015 |
| WO | 2016193346 A1 | 12/2016 |

OTHER PUBLICATIONS

International Search Report issued for PCT/EP2016/062395 dated Aug. 8, 2016.

* cited by examiner

HOUSING FOR MOUNTING A CONTAINER ON AN INJECTION PEN, ASSEMBLY FORMING AN INJECTABLE PRODUCT RESERVOIR FOR AN INJECTION PEN AND INJECTION PEN EQUIPPED WITH SUCH AN ASSEMBLY

This application is a National Stage application of PCT international application PCT/EP2016/062395, filed on Jun. 1, 2016 which claims the priority of French Patent Application No. 15 54993, filed on Jun. 2, 2015, both of which are incorporated herein by reference in their entirety.

The invention relates to a housing for mounting an elongated container on an injection pen. The invention also relates to an assembly forming an injectable product reservoir for an injection pen, as well as an injection pen equipped with such an assembly.

The invention belongs to the field of injection pens used to inject an active ingredient parenterally, i.e., intravenously, subcutaneously or intramuscularly, into a patient's body. Such a pen can be used to treat a patient with a specific disease, such as diabetes or dwarfism. Indeed, the treatment of such a patient requires at least one injection per day, of insulin in the case of diabetes or growth hormone in the case of dwarfism. In light of the number of injections needed, patients often perform their injections themselves, without the assistance of a healthcare provider.

To that end, patients increasingly frequently use an injection pen, which is easier to use than a traditional syringe, since it can be stored discreetly and safely. An injection pen is implemented with containers, most often called "cartridges", with relatively small holding capacities and nevertheless making it possible to perform a certain number of injections. A cartridge is a cylindrical container with a circular section, the length of which is about 60 mm and the outer diameter of which is comprised between 8.5 and 12 mm, preferably about 11 mm. Such an injection pen is easy for the patient to transport, like a traditional pen.

To use such an injection pen, the latter must be equipped with a container containing the active ingredient to be injected, namely a capsule or cartridge as set out above. Before each use, a needle must be mounted at the distal end of the container, this needle being thrown away after use, while the container remains on the injection pen. The container should therefore be kept in position on a base of the injection pen.

To that end, it is known from US-A-2014/0358093 to provide, at the front of the base of an injection pen, a cartridge support suitable for receiving a cartridge full of active ingredient to be injected. The immobilization of each cartridge in this support takes place using a coupling element that is mounted around one end of the cartridge and that is provided to cooperate with the cartridge support. This coupling element leaves the majority of the cartridge exposed, while the latter is not mounted within the injection pen, resulting in a non-negligible risk of this cartridge breaking, the contents of which are then lost, which prevents treatment.

It is furthermore known from WO-A-2013/124,118 to use jaws arranged at the end of flexible arms to retain a cartridge of active ingredient inside a support of an injection pen. This equipment is relatively complex to use, in particular by a patient who may be weakened or unfamiliar with these manipulations.

Figure 6:
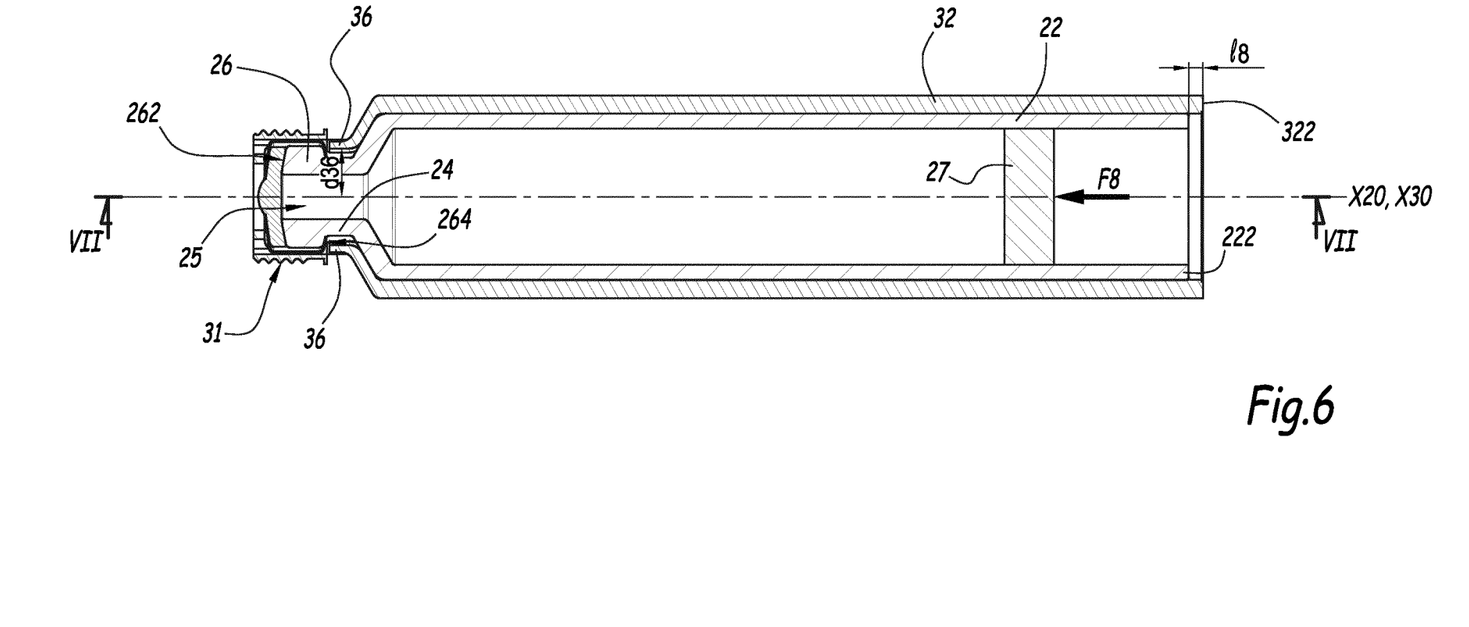
FIG. 6 is a sectional view along line VI-VI in FIG. 5.

Furthermore, WO-A-2012/017063 teaches, in one embodiment shown in FIG. 6, using a slotted ring to retain a container in a housing. This slotted ring can be compressed to remove the container from the housing, such that the obtained blocking is not irreversible. In another embodiment shown in FIGS. 9 and 10, the immobilization of the container in a housing is done from the rear. This requires that the dimensions of the container be fully controlled so that it can cooperate with fastening means provided at the rear of the housing, which is in practice not possible in light of the machining allowances of the containers and housings. Lastly, in other embodiments shown in FIGS. 14 to 18, a staple is attached on a housing to jam a container in a housing. Like the slotted ring of the embodiment of FIG. 6, this staple is a separate part from the body of the housing, which should be produced and procured separately and the placement of which is difficult in the context of industrial production.

Lastly, WO-A-2011/092326 discloses a housing for receiving a container of the cartridge type, this housing being equipped with fastening elements configured so as not to interfere with the container as long as a hollow needle has not been mounted on the housing to exert, on an extension of each fastening element, a centripetal force to fold this fastening element down radially toward the inside. Thus, no blocking of a container in the housing can be obtained as long as the hollow needle is not in place. Furthermore, the obtained blocking is not irreversible, since it suffices to disassemble the hollow needle, which may in practice be done after each injection, so that the fastening elements regain their original geometry and the container is released.

The invention more particularly aims to resolve these drawbacks by proposing a new approach for mounting a container such as a capsule or cartridge on an injection pen.

To that end, the invention relates to a housing for mounting an elongated container on an injection pen, wherein this mounting housing comprises an elongated body that extends along a longitudinal axis and defines an inner volume for fully receiving the container. The body is provided, on the outside of a first axial end, with at least one first mechanical member for attaching a needle and, in the vicinity of a second axial end opposite the first axial end, with at least one second mechanical member for attaching the housing onto an injection pen. According to the invention, the housing comprises, in the vicinity of its first end, at least one third mechanical member for irreversibly locking a container in position, fully contained in the inner volume of the body. Furthermore, the third member is an elastically deformable tab of the housing, which is intended to ensure irreversible locking of the container in position in the inner volume of the body of the housing, by axially retaining a flange of the container.

Owing to the invention, the housing makes it possible to protect the container effectively, particularly when it involves a cartridge, over its entire length, while preventing the injection pen with which the container is provided to cooperate from being equipped with a support member having a relatively complex shape, since it is the housing itself that ensures the fastening of the container on a base of the injection pen. Furthermore, the second mechanical member can be configured as a function of the injection pen on which the container is provided to be mounted, which prevents handling errors, since the housing then serves as a mistake-proofing means for mounting the container on the injection pen. Lastly, the third mechanical member ensures the irremovable nature of the assembly between the housing and a container and, consequently, the sustainability of the protection imparted by the housing to a container. In particular, the fact that this third mechanical member is made up of an elastically deformable tab of the housing prevents the use of an appendage, such as a slotted ring or a staple.

According to advantageous but optional aspects of the invention, such a housing may incorporate one or more of the following features, considered in any technically allowable combination:

- In the unstressed configuration, the tab extends at a radial distance from the longitudinal axis smaller than half the inner diameter of the first axial end.
- The tab comprises an edge opposite the second axial end of the housing and that is intended to axially and irreversibly lock the flange of the container.
- The tab forms a single piece with the body.
- The tab is surrounded by a U-shaped cutout with a flat bottom, the bottom of which delimits the edge of the tab opposite the second axial end.
- The housing comprises two diametrically opposite tabs relative to the longitudinal axis.
- The or each tab is configured to be pushed radially back toward the outside of the first axial end by part of a container during irreversible mounting in the housing.
- The body is at least partially made from a transparent material.
- The first mechanical fastening member comprises a thread and/or a bayonet locking relief.
- The second mechanical fastening member comprises a thread, a tapping and/or a bayonet locking relief.

Furthermore, the invention relates to an assembly forming an injectable product reservoir for an injection pen, this assembly comprising an elongated container containing an injectable product, as well as a housing as mentioned above, while the container is fully housed in the inner volume of the body of this housing.

Such an assembly can be manipulated in a unitary manner, in particular for transport and mounting on an injection pen, while the container is effectively protected from impacts and risks of pollution due to the fact that it is fully housed in the inner volume of the body of the housing.

According to advantageous but optional aspects of the invention, such an assembly may incorporate one or more of the following features, considered in any technically allowable combination:

- The second end extends, along the longitudinal axis of the body and over a nonzero distance, past the container.
- The container is equipped with a flange, which surrounds a mouth of the container, while the elastically deformable tab is positioned across from, or bearing against, an axial surface of the flange, oriented opposite the mouth of the container.
- The container is equipped with a stopper and a cap surrounding the stopper, which are inserted into the first axial end of the housing.
- Alternatively, the housing is provided with a recess for receiving a stopper independently of the container, while the container has no cap surrounding the stopper.

Lastly, the invention relates to an injection pen, intended to be used to inject an active ingredient into the body of a patient and which comprises a base intended to be held by a user, as well as a removable injectable product reservoir. According to the invention, this injectable product reservoir is formed by an assembly as mentioned above, while the second mechanical member of the body of the housing is engaged with a complementary mechanical member arranged on the base.

The invention will be better understood, and other advantages thereof will appear more clearly, in light of the following description of two embodiments of a housing, an assembly forming a reservoir and an injection pen according to its principle, provided solely as an example and done in reference to the appended drawings, in which.

Figure 1:
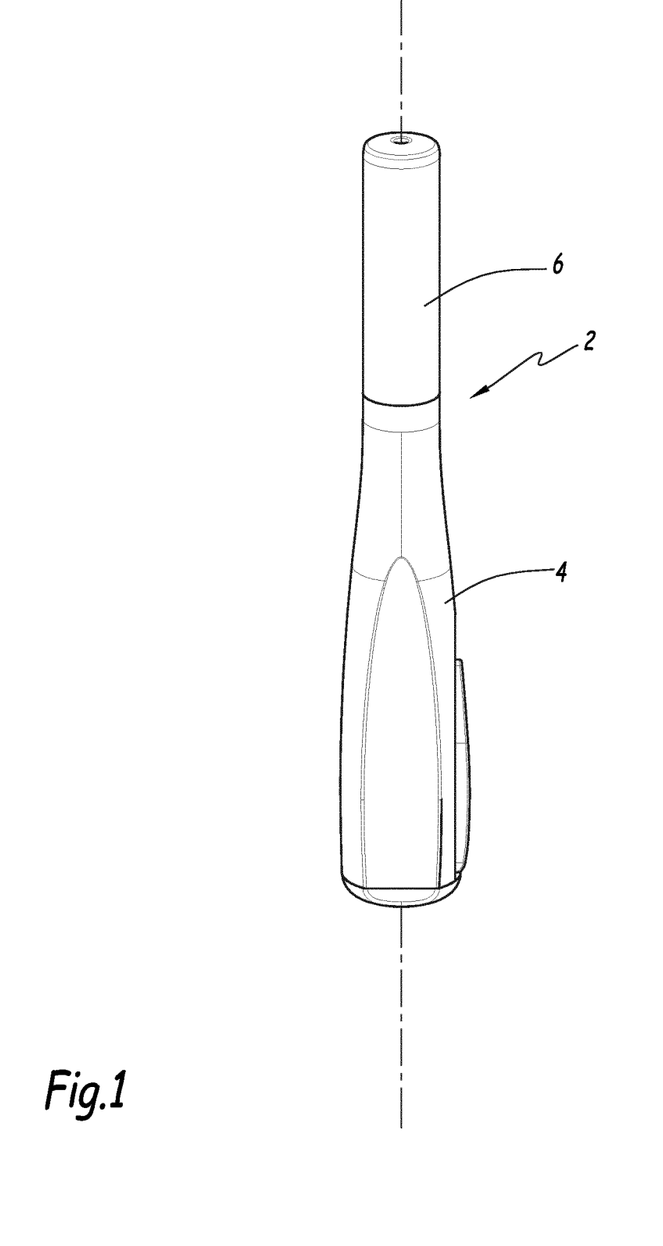
FIG. 1 is a perspective view of an injection pen according to the invention, in a storage or transport configuration.
Figure 2:
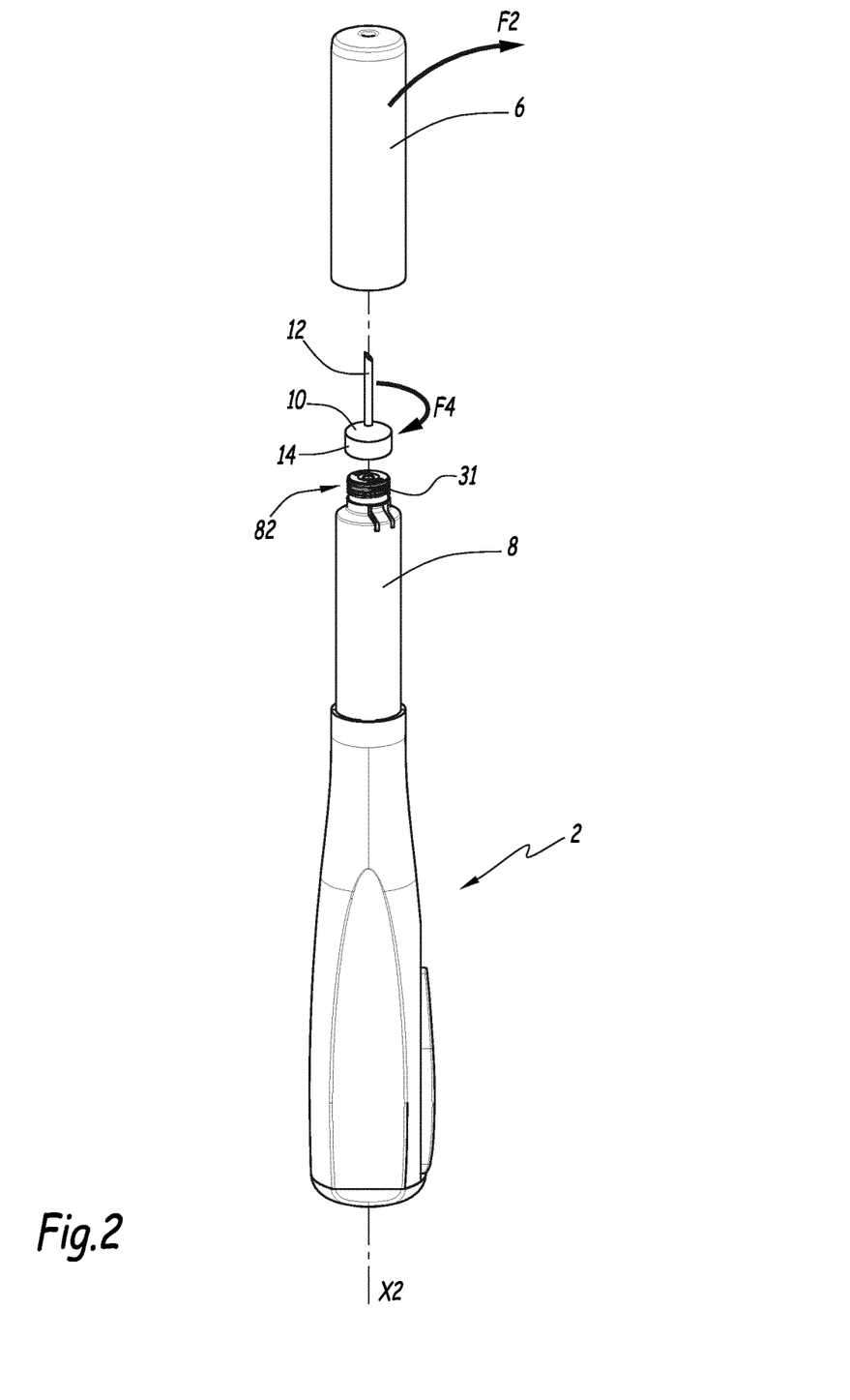
FIG. 2 is a perspective view of the pen of FIG. 1 in a pre-use configuration.
Figure 3:
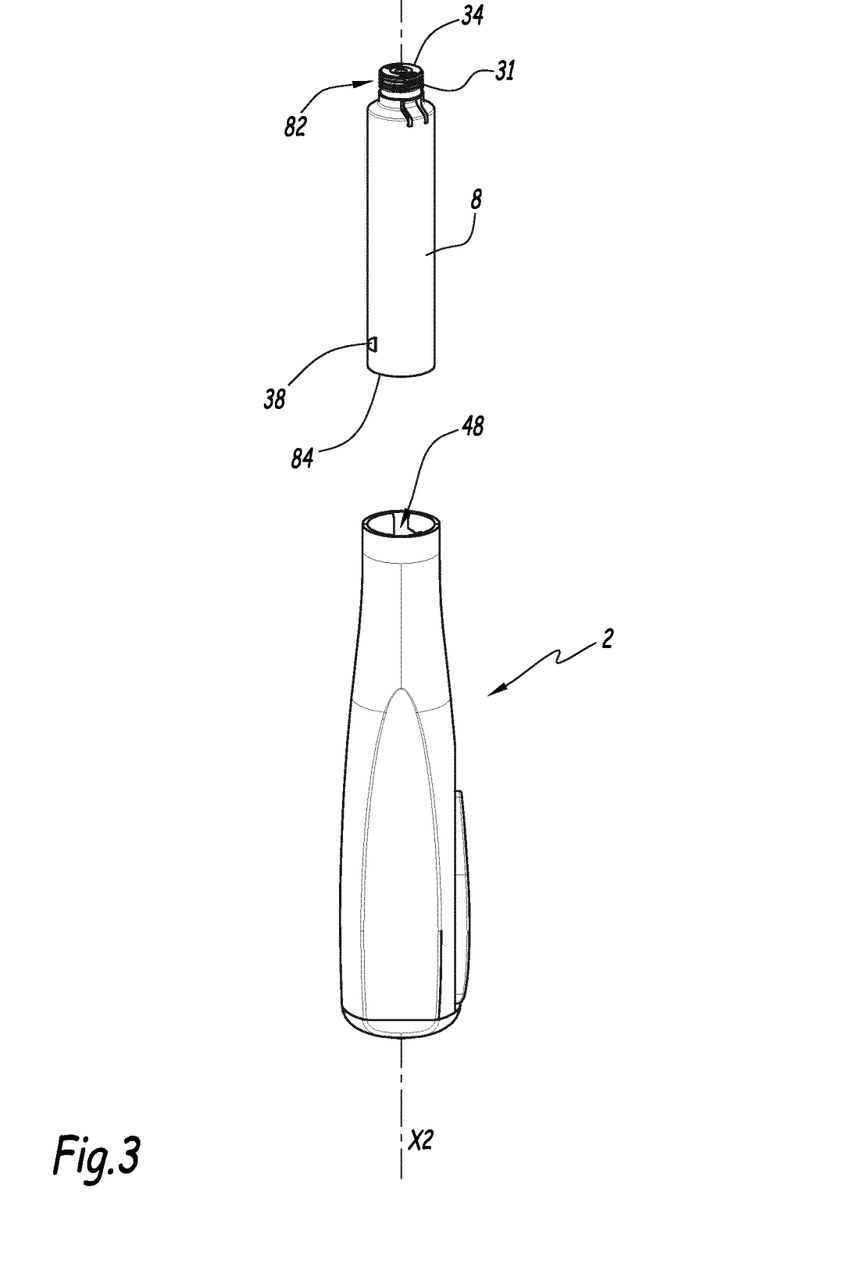
FIG. 3 is a perspective view similar to FIG. 1 in a configuration for changing an assembly forming a reservoir of injectable product for the injection pen of FIGS. 1 and 2.

The injection pen 2 visible in FIGS. 1 to 3 extends along a longitudinal axis X2 and comprises a base 4, intended to be held by a user during an injection, as well as a cover 6 attached on the base 4 and which, when it is in place on this base 4, isolates a reservoir-forming assembly 8 from the outside, the latter in turn being mounted on the base 4, as shown by the following explanations.

The assembly 8 contains an injectable product, in particular a drug containing an active ingredient intended to treat a disease requiring treatment by regular doses, such as diabetes or dwarfism.

As shown in FIG. 2, when the injection pen 2 needs to be used, the cover 8 is removed, which is shown by arrow F2, and a disposable element 10, comprising the needle 12, is mounted at the distal end 82 of the assembly 8, which is shown by arrow F4. To that end, the distal end 82 is provided with an outer thread 31, while a base part 14 of the assembly 10 is equipped with an inner tapping with a corresponding geometry, not visible in FIG. 2. Thus, a disposable element 10 can be screwed on the distal end 82 before each use of the injection pen 2, its needle 12 then being aligned on the axis X2.

The reservoir-forming assembly 8 is shown alone in FIGS. 4 to 9. Two elements are formed, i.e., a carpule or cartridge 20 and a housing or enclosure 30 that is provided on the one hand to contain the cartridge 20, and on the other hand to allow, at the distal end 82, fastening thereof with the disposable element 10, and a proximal end 84 of the assembly 8, fastening thereof on the base 4.

The cartridge 20 is made from glass and forms an elongated container centered on a longitudinal axis X20 and having a cylindrical body 22 with a circular section, the outer diameter D22 of which is comprised between 8.55 and 12 mm. Alternatively, the cartridge 20 may be made from plastic. This cartridge is provided with a neck 24 defining a throat 25 through which it is possible to fill the cartridge or to remove an injectable product therefrom and that is surrounded by a flange 26, for which reference 262 denotes an annular surface surrounding the outlet of the throat 25 and reference 264 denotes an annular surface oriented away from the surface 262 and turned toward an end 222 of the body 22 opposite the throat 25.

Hereinafter, a direction is said to be axial when it is parallel to an axis and radial when it is perpendicular and secant to said axis. A surface is said to be axial when it is perpendicular to an axial direction and radial when it is perpendicular to a radial direction.

The surfaces 262 and 264 are axial surfaces relative to the axis X20.

The end 222 of the body 22 is open and a piston 27 is housed in the body 22, through this end 222, with a possibility of axial sliding along the axis X20. The axial sliding of the piston 27 in the body 22 is commanded by means integrated into the base 4, which are known in themselves and are not described here in detail.

A stopper device 29 is mounted on the body 22, on the side of the neck 24, and comprises a stopper 292 formed by an elastomeric washer that is circular and pressed on the surface 262. The stopper device 29 also comprises a cap 294, which may be made from aluminum or made by molding plastic and which immobilizes the stopper 292 on the flange 26.

The housing 30 is centered on a longitudinal axis X30 and comprises a body 32 made by molding plastic, for example polycarbonate.

The body 32 defines an inner volume V32 in which the cartridge 20 can be fully received. In other words, the cartridge 20 can be housed in the volume V32 without protruding outside the body 32 of the housing 30.

The body 32 comprises a main part 33, the inner diameter d33 of which is slightly larger than the diameter D22. Slightly larger means that the diameter d33 is less than 110% of the diameter D22. The body 32 also comprises a head 34, in one piece with the main part 33 and intended to receive the flange 26 equipped with the stopper device 29. The head 34 forms the distal end 82 of the assembly 8.

At the junction between the main part 33 of the body 32 and the head 34, the housing 30 is provided with two elastically deformable tabs 36 that are also in one piece with the rest of the body 32. The tabs 36 are each surrounded by a U-shaped cutout 37 with a flat bottom. As shown in FIG. 6, the tabs 36 are diametrically opposite relative to the axis X30.

Reference 322 denotes the open end of the body 32 opposite the head 84, and reference 362 denotes the edge of each tab 36 oriented opposite the end 322. The end 322 forms the proximal end 84 of the assembly 8.

The body 32 has no window or opening. In other words, the body 32 is continuous around the axis X30, such that it completely isolates the volume V32 from the outside, except at the open end 322.

The head 34 is provided with a bottom 342 that defines a central opening 344 centered on the axis X30 and that provides access to the stopper 292 in the configuration with the cartridge 20 mounted in the housing 30. The inner diameter d34 of the head 34, defined in a part of this head 34 comprised between the bottom 342 and the edges 362 of the tabs 36, is slightly larger than the outer diameter D26 of the flange 26 surrounded by the cap 294, with a ratio d34/D26 below 1.05.

Figure 5:
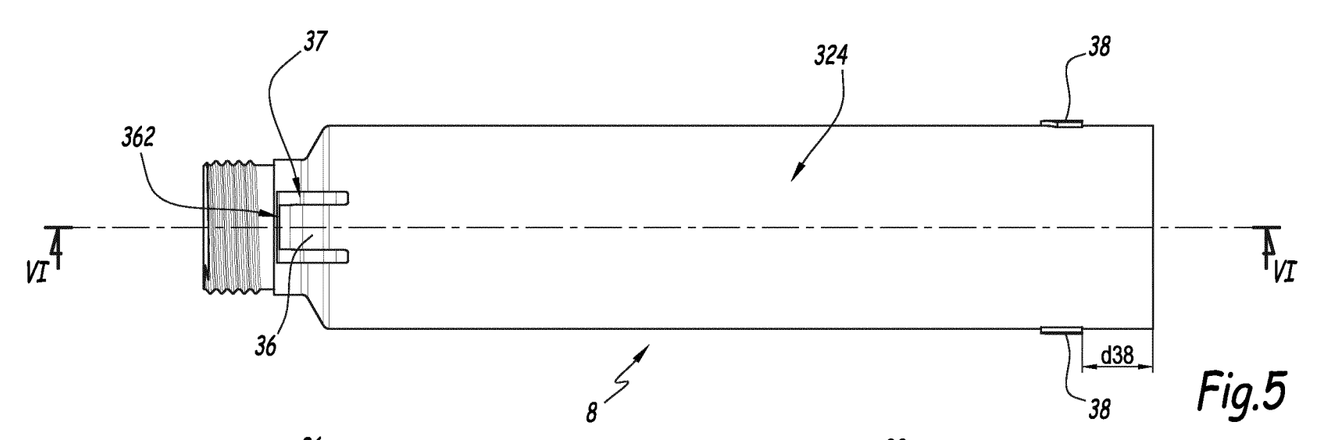
FIG. 5 is a side view of the reservoir-forming assembly of FIG. 4.

As shown in particular in FIGS. 5 and 6, each tab 36 extends, parallel to the axis X30, from the end 322 toward the bottom 342, with its edge 362 turned toward this bottom.

In the unstressed configuration, i.e., without outside force applied thereon, the tabs 36 extend at a radial distance d36 from the axis X30 smaller than half the diameter d34. In other words, the tabs 36 protrude radially toward the inside of the volume V32 relative to the rest of the head 34.

Furthermore, and as emerges more particularly from FIGS. 4, 5, 7 and 8, the body 32 bears, on its outer radial surface 324 and near the end 322, two pins 38 protruding radially relative to the surface 324 and that are diametrically opposite. The axial distance d38 between the pins 38 and the end 322 is smaller than 10 mm. Each pin 38 is intended to cooperate with a groove of the base 4, only one of which is shown in FIG. 3 with reference 48. Each groove 48 comprises a longitudinal branch, parallel to the axis X2, and a branch that is transverse or inclined relative to this axis. Thus, the elements 38 and 48 together constitute a bayonet locking system for the housing 30, and thus the assembly 8, on the base 4.

Figures 4, 8:
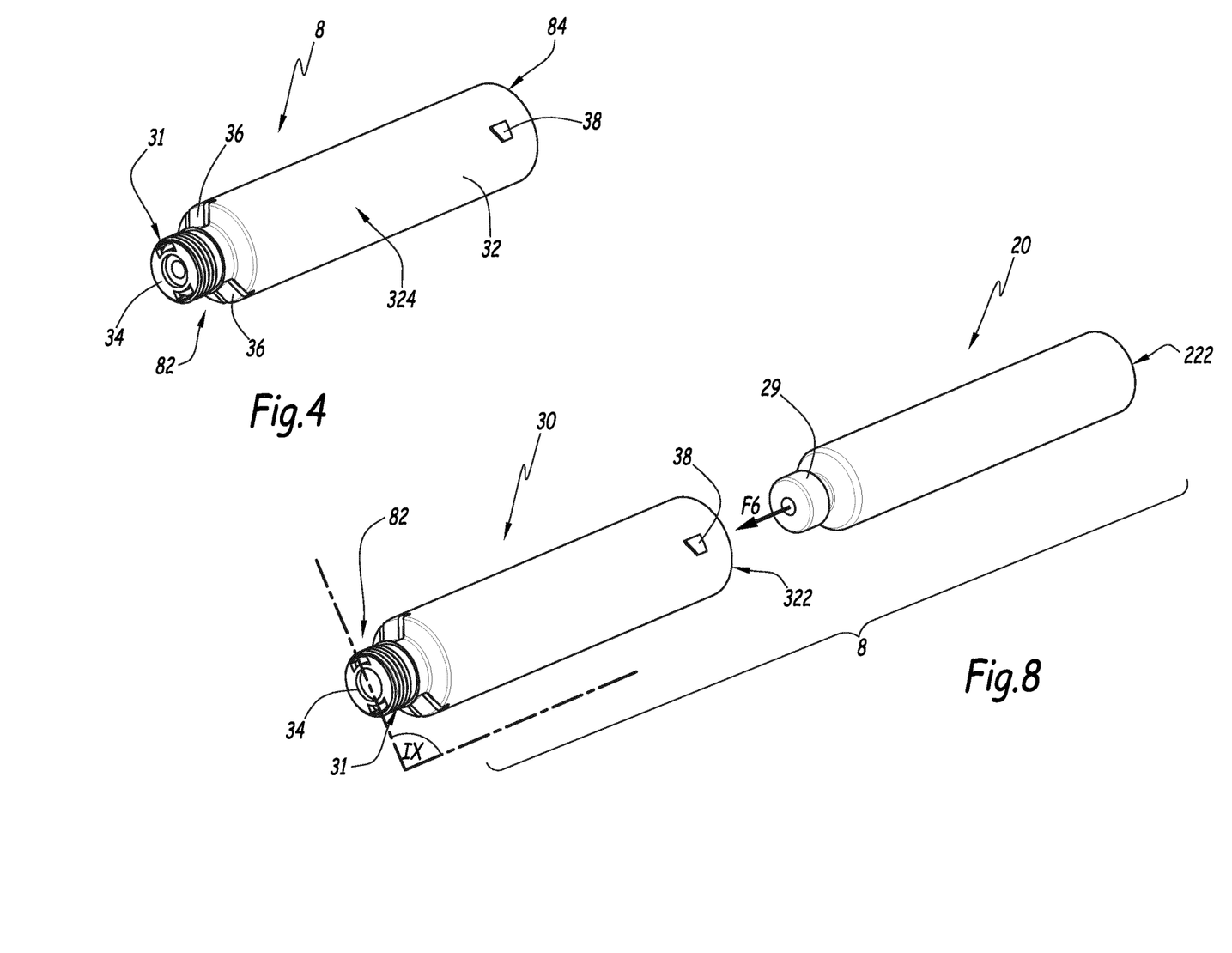
FIG. 4 is a perspective view, from another angle, of the reservoir-forming assembly visible in FIGS. 2 and 3.
FIG. 8 is an exploded perspective view of the reservoir-forming assembly during assembly.
Figure 9:
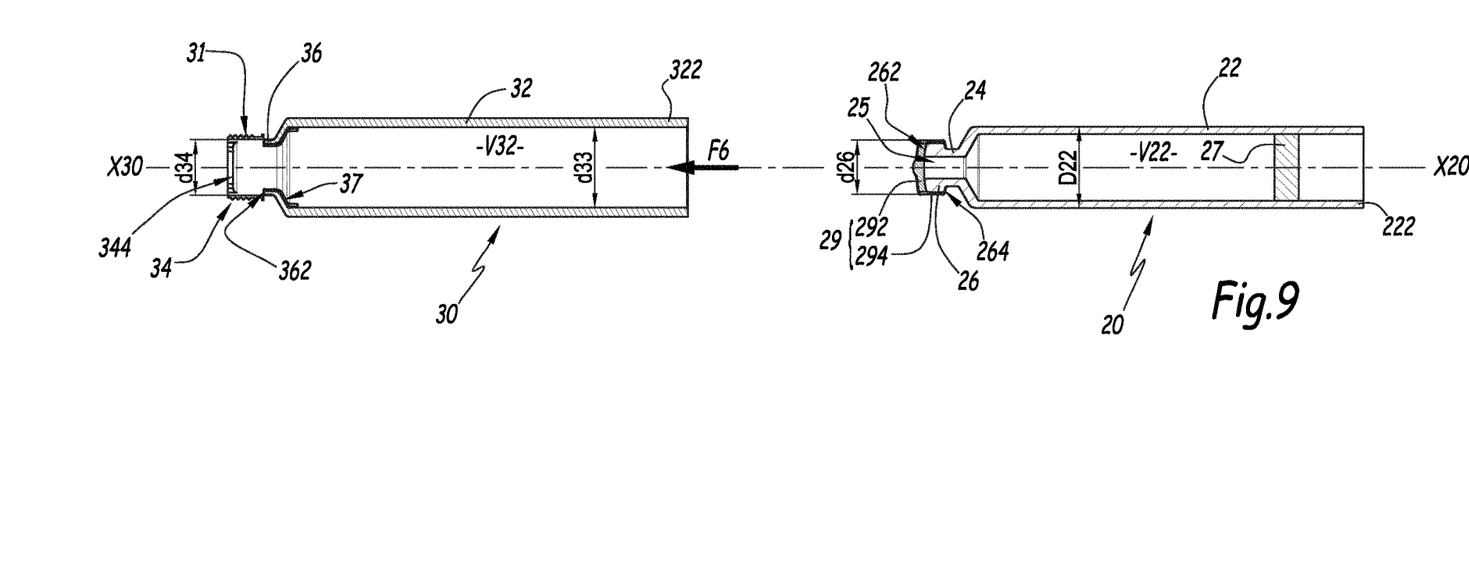
FIG. 9 is a sectional view along plane IX in FIG. 8, on a smaller scale than FIGS. 6 and 7.

When the cartridge 20 needs to be mounted in the housing 30, the axes X20 and X30 are aligned and the cartridge 20 is pushed into the volume V32, in the direction of arrow F6 in FIGS. 8 and 9 until the stopper device 29 abuts against the bottom 342 of the head 34. In passing, the cap 294 radially pushes the tabs 36 back toward the outside of the head 34, these tabs being able to move radially away from the axis X30 due to their elasticity. When the cap 294 comes into contact with the bottom 342, the flange 26 has axially exceeded, along the axis X30, the tabs 36, which are then positioned, along this axis, at the neck 24, with their respective edges 362 across from or bearing against the surface 264 of the flange 26 and the part of the cap 294 that covers this surface. Thus, the cartridge 20 is axially locked in the body 32 of the housing 30, irreversibly.

The assembly 8 is thus formed and can be manipulated by a user in a unitary manner.

Figure 7:
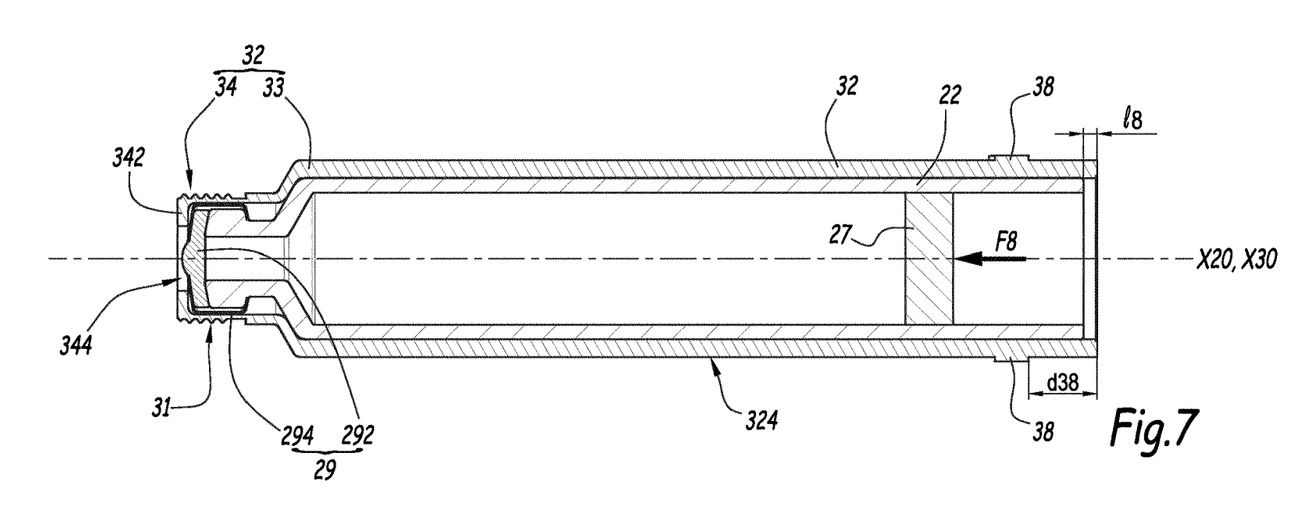
FIG. 7 is a sectional view along line VII-VII in FIG. 6.

As emerges from FIGS. 6 and 7, the end 222 of the body 22 is withdrawn, inside the body 32. In practice, a distance l8 separates the ends 222 and 322 along the axes X20 and X30. Thus, the end 322 extends, along these axes, past the cartridge 20, which is effectively protected from impacts, in particular when the reservoir-forming assembly 8 is placed on a vertical surface with its distal end 82 oriented upward.

In practice, when an assembly 8 has been used on the injection pen 2, to the point that its cartridge 20 is empty or practically empty, this assembly 8 can be removed from the base 4 via a rotational movement around the axes X2, X20 and X30, then combined, and a translational movement parallel to this axis making it possible to unlock the bayonet system formed by the elements 38 and 48. Next, a new reservoir-forming assembly 8, the cartridge 20 of which is full, can be mounted on the base 4, through a new translation/rotation movement activating the bayonet system.

In this case, the assembly 8 previously disassembled from the injection pen 2 is discarded. In other words, the elements 20 and 30 are disposable after use, which is consistent with the fact that the locking of the cartridge 20 in the housing 30 is irreversible.

The outer thread 31 is formed on the periphery of the head 34 and makes it possible to mount, successively on the assembly 8 in place on the base 4, disposable elements 10 each time a dose of the product contained in the cartridge 20 must be injected in a patient. The mounting of the disposable element 10 on the distal end 82 of the assembly 8 formed by the head 34 results in perforating the stopper 292 through the opening 344. When the disposable element 10 is in place on the assembly 8, a pushing force, oriented toward the head 34, is exerted on the piston 27 as shown by arrows F8 in FIGS. 6 and 7, in order to drive part of the product present in the inner volume V22 of the body 22 toward the needle 12 of the disposable element 10.

The body 32 is transparent, at least at its main part that surrounds the body 22. This makes it possible to view, through the body 32, a sticker affixed on the body 22, in order to verify that the product contained in the volume V22 is appropriate with respect to the treatment prescribed for the patient and the type of injection pen 2 being used.

The body 32 is not necessarily completely transparent. Only part of the latter may be transparent, in an area making it possible to view a sticker affixed on the cartridge 20, as well as the product level remaining in this cartridge.

Furthermore, the geometry and positioning of the pins 38 can be configured based on the geometry and positioning of the grooves 48. This makes it possible to pair a type of reservoir-forming element 8 with a type of injection pen 2. One thus avoids the risks of incorrect handling, which would consist of mounting an assembly 8 on an injection pen 2 that is not suitable for said injection pen, for example because the volume V22 has a diameter different from that for which the linear movement of the pushing means on the piston 27 is calculated. In particular, the pins 38 and grooves 48 are not necessarily diametrically opposite.

Figure 10:
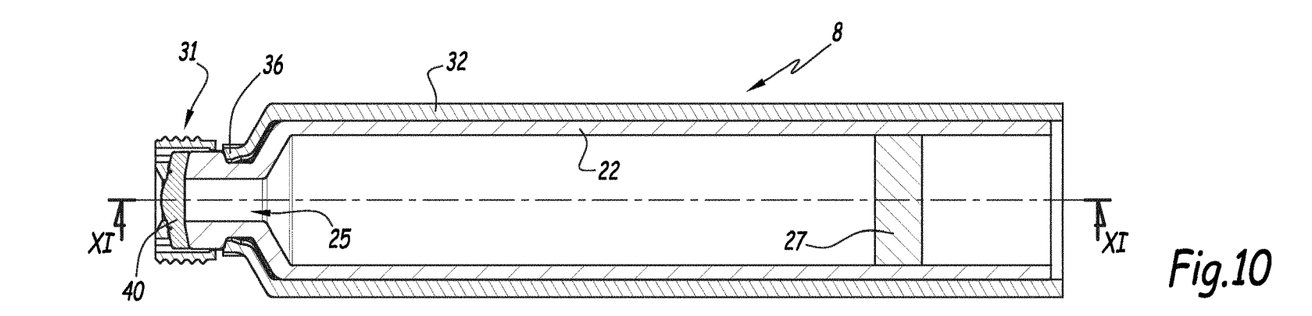
FIG. 10 is a sectional view similar to FIG. 6 for a reservoir-forming assembly according to a second embodiment of the invention.
Figure 11:
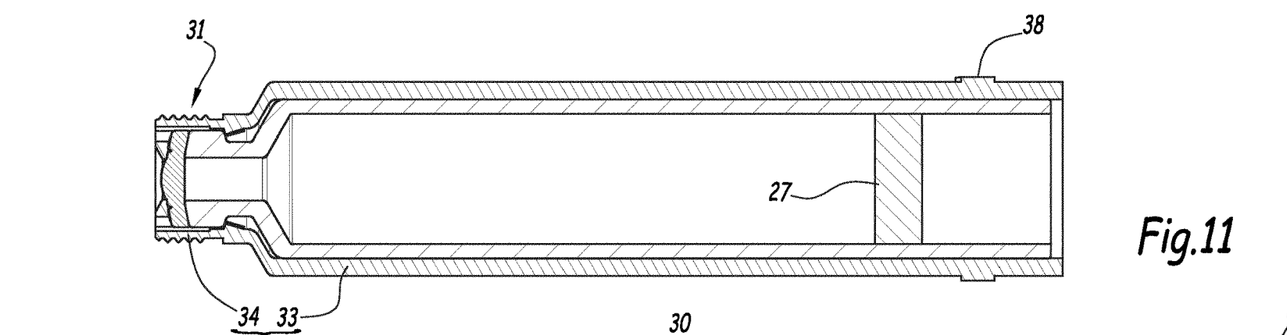
FIG. 11 is a cross-section along line XI-XI in FIG. 10.
Figure 12:
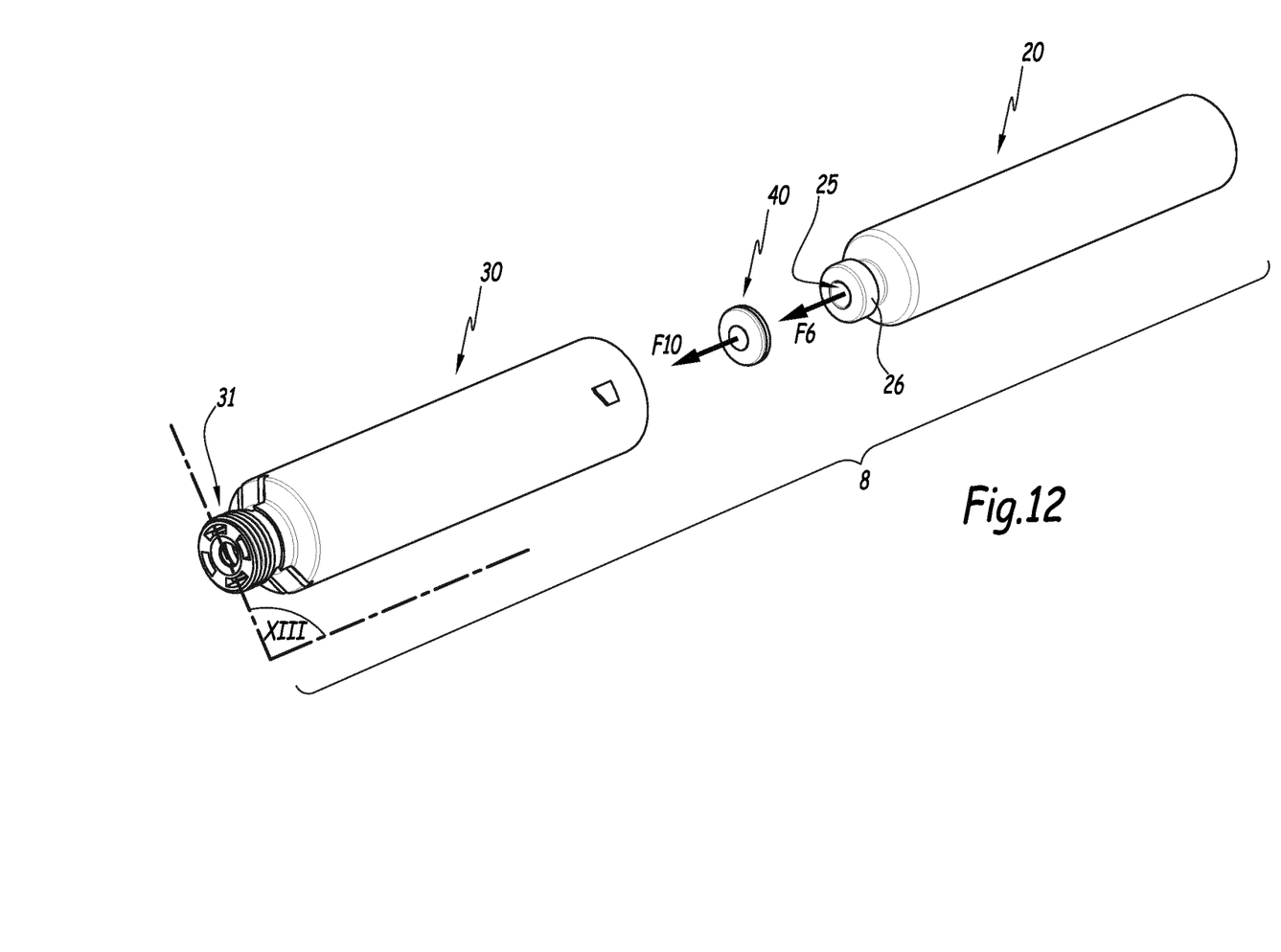
FIG. 12 is an exploded perspective view of the reservoir-forming assembly of FIGS. 10 and 11 during assembly.

In the second embodiment of the invention shown in FIGS. 10 to 12, the elements similar to those of the first embodiment bear the same references. Below, we describe primarily what differs from the preceding embodiment.

In this embodiment, the cartridge 20 has no stopper device before it is mounted in the housing 30. In particular, no cap comparable to the cap 294 is used in this second embodiment.

Figure 13:
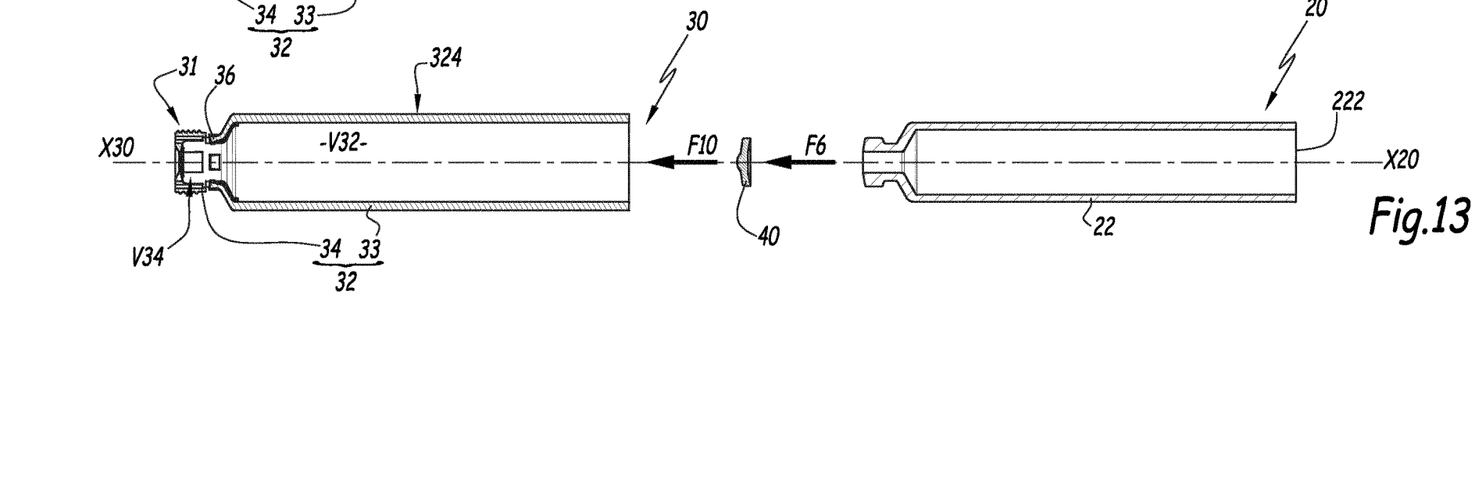
FIG. 13 is a sectional view along plane XIII in FIG. 12, on a smaller scale than FIGS. 10 and 11.

In this embodiment, a stopper 40 is placed in the head 34 of the housing 30 before the cartridge 20 is inserted into the volume V32. More specifically, the head 34 forms a volume V34 for receiving and jamming of the stopper 40, as shown in FIG. 13. The volume V34 is part of the volume V32. The assembly of the reservoir-forming assembly 8 according to this second embodiment is done by first inserting the stopper 40 into the head 34, in the direction of arrows F10 in FIGS. 12 and 13, then inserting the cartridge 20 with no stopper device or piston into the volume V32, as shown by arrows F6 in FIGS. 12 and 13.

Alternatively, the stopper 40 can be overmolded in the housing 30 during its manufacture. It is then not necessary to perform the insertion along arrows F10.

One then forms a reservoir-forming assembly 8 that is empty and that can be filled through the end 222 of the body 22 of the cartridge 20 before placement of the piston 27.

The reservoir-forming assembly 8 of this second embodiment, once filled and equipped with its piston, can be used like that of the first embodiment.

In particular, it comprises a thread 31 allowing the mounting of a disposable element 10 and pins 38 making it possible to fasten it on the base 4 of an injection pen 2.

In this case, since the cartridge 20 is filled while already in place in the body 30, the sticker for the product can be placed on the outer radial surface 324 of the body 32, which is not necessarily transparent, even though this is advantageous to make it possible to view the product level remaining in the cartridge 20, like for the first embodiment.

Irrespective of the embodiment, the thread 31 constitutes a mechanical member for fastening the needle 12 on the housing 30. Alternatively, other types of mechanical members can be considered to perform this function, in particular lugs allowing the disposable element 20 to be mounted via a bayonet system.

Likewise, irrespective of the embodiment, the pins 38 constitute mechanical members for fastening the housing 30 on the base 4. Alternatively, they can be replaced by other mechanical members performing the same function, for example a thread arranged on the surface 324, as long as the base 4 is equipped with a corresponding tapping. Furthermore, if the body 32 protrudes enough from the body 22 on the side of the proximal end 84 of the element 8, a tapping can be provided on the inner surface of the body 32 while a corresponding thread is provided on the base 4.

In the bayonet system(s) used, the male and female reliefs, i.e., the pins 38 and the grooves 48, are positioned on the housing 30 or on the base 40, as chosen.

The embodiments and alternatives considered above may be combined to generate new embodiments of the invention.

The invention claimed is:

1. A housing for mounting an elongated container on an injection pen, this mounting housing comprising an elongated body that extends along a longitudinal axis and that defines an inner volume for receiving the container fully, while the body is provided, on the outside of a first axial end, with at least one first mechanical member for attaching a needle and, in the vicinity of a second axial end opposite the first axial end, with at least one second mechanical member for attaching the housing onto an injection pen; wherein
the housing comprises, in the vicinity of its first axial end, at least one third mechanical member for irreversibly locking a container in position, fully contained in the inner volume of the body, and
the third member is an elastically deformable tab of the housing, which is in a single piece with the body wherein when the third member is in an unstressed configuration the tab ensures irreversible locking of the container in position in the inner volume of the body of the housing, by axially retaining a flange of the container.

2. The housing according to claim 1, wherein, in the unstressed configuration, the tab extends at a radial distance from the longitudinal axis smaller than half the inner diameter of the first axial end.

3. The housing according to claim 1, wherein the tab comprises an edge opposite the second axial end of the housing and that is intended to axially and irreversibly lock the flange of the container.

4. The housing according to claim 3, wherein the tab is surrounded by a U-shaped cutout with a flat bottom, the bottom of which delimits the edge of the tab opposite the second axial end.

5. The housing according to claim 1, wherein it comprises two diametrically opposite tabs relative to the longitudinal axis.

6. The housing according to claim 1, wherein the tab is configured to be pushed radially back toward the outside of the first axial end by part of a container during irreversible mounting in the housing.

7. The housing according to claim 1, wherein the body is at least partially made from a transparent material.

8. The housing according to claim 1, wherein:
the first mechanical fastening member comprises a thread and/or a bayonet locking relief, and/or
the second mechanical fastening member comprises a thread, a tapping and/or a bayonet locking relief.

9. An assembly forming an injectable product reservoir for an injection pen, wherein it further comprises a housing according to claim 1 and wherein the container is fully housed in the inner volume of the body of the housing.

10. The assembly according to claim 9, wherein the second end extends, along the longitudinal axis of the body and over a nonzero distance, past the container.

11. The assembly according to claim 9, wherein the container is equipped with a flange, which surrounds a mouth of the container, and wherein the elastically deformable tab is positioned across from, or bearing against, an axial surface of the flange, oriented opposite the mouth of the container.

12. The assembly according to claim 9, wherein the container is equipped with a stopper and a cap surrounding the stopper, which are inserted into the first axial end of the housing.

13. The assembly according to claim 9, wherein the housing is provided with a recess for receiving a stopper independently of the container, while the container has no cap surrounding the stopper.

14. The assembly according to claim 9, wherein the elongated container and the housing are disposable after use.

15. An injection pen, intended to be used to inject an active ingredient into the body of a patient and comprising:
 a base intended to be held by a user,
 a removable injectable product reservoir,
wherein the removable injectable product reservoir is formed by an assembly according to claim 9, and wherein the second mechanical member of the body of the housing is engaged with a complementary mechanical member arranged on the base.

* * * * *